United States Patent
Jacobs et al.

(10) Patent No.: US 9,251,493 B2
(45) Date of Patent: Feb. 2, 2016

(54) MEDICATION VERIFICATION AND DISPENSING

(75) Inventors: Alan Jeffrey Jacobs, Palo Alto, CA (US); Eugene Gershtein, Redwood City, CA (US)

(73) Assignee: PerceptiMed, Inc., Palo Alto, CA (US)

( * ) Notice: Subject to any disclaimer, the term of this patent is extended or adjusted under 35 U.S.C. 154(b) by 351 days.

(21) Appl. No.: 13/583,598

(22) PCT Filed: Mar. 8, 2011

(86) PCT No.: PCT/US2011/027586
§ 371 (c)(1),
(2), (4) Date: Sep. 7, 2012

(87) PCT Pub. No.: WO2011/112606
PCT Pub. Date: Sep. 15, 2011

(65) Prior Publication Data
US 2012/0330684 A1  Dec. 27, 2012

Related U.S. Application Data

(60) Provisional application No. 61/311,900, filed on Mar. 9, 2010.

(51) Int. Cl.
*G06Q 50/22* (2012.01)
*G06Q 10/08* (2012.01)
(Continued)

(52) U.S. Cl.
CPC . *G06Q 10/08* (2013.01); *A61J 7/04* (2013.01); *G06F 19/3462* (2013.01);
(Continued)

(58) Field of Classification Search
CPC ....... G06Q 50/22; G06Q 50/24; G06Q 40/08; G06Q 10/10; G06F 19/322
See application file for complete search history.

(56) References Cited

U.S. PATENT DOCUMENTS

| 5,363,968 A | 11/1994 | Soloman |
| 5,502,944 A | 4/1996 | Kraft et al. |

(Continued)

FOREIGN PATENT DOCUMENTS

| CN | 1063373 A | 8/1992 |
| JP | H08-322912 A | 12/1996 |

(Continued)

OTHER PUBLICATIONS

European Extended Search Report, European Application No. 11753941.1, Aug. 28, 2013, 6 pages.
(Continued)

*Primary Examiner* — Tran Nguyen
(74) *Attorney, Agent, or Firm* — Fenwick & West LLP

(57) ABSTRACT

Medication errors happen frequently in hospital, home, and pharmacy environments. A medication verification and dispensing system provides protection against such errors. The apparatus includes a guide tube that receives a medication and imaging device(s) adjacent to the guide tube that take image(s) of the medication. The imaging devices(s) and light source(s) are oriented for capturing images that reveal markings, color, size, shape, etc., of the medication. A verification system uses a signature of the image to identify the medication or compares the image(s) to reference images to identify the medication and to a prescription record of the patient to ensure it is a correct medication, dose, amount, timing, etc., for administration. If the medication is correct, it is dispensed into a dispensing vessel that locks the medication inside, but unlocks when it recognizes a unique patient identifier worn by a patient that is a correct recipient for the medication.

59 Claims, 9 Drawing Sheets

(51) Int. Cl.
*A61J 7/04* (2006.01)
*G06F 19/00* (2011.01)
*G07F 11/00* (2006.01)
*G07F 11/44* (2006.01)
*G07F 17/00* (2006.01)
*G06Q 50/10* (2012.01)
*A61J 7/00* (2006.01)
*A61J 1/03* (2006.01)

(52) U.S. Cl.
CPC ............ *G06Q 50/22* (2013.01); *G07F 11/005* (2013.01); *G07F 11/44* (2013.01); *G07F 17/0092* (2013.01); *A61J 1/03* (2013.01); *A61J 7/0046* (2013.01); *A61J 7/0084* (2013.01); *A61J 7/0427* (2013.01); *A61J 2200/30* (2013.01); *A61J 2205/60* (2013.01)

(56) References Cited

U.S. PATENT DOCUMENTS

| | | | |
|---|---|---|---|
| 5,700,998 A | 12/1997 | Palti | |
| 6,535,637 B1 | 3/2003 | Wootton et al. | |
| 6,771,369 B2 | 8/2004 | Rzasa et al. | |
| 7,028,723 B1 | 4/2006 | Alouani et al. | |
| 7,348,884 B2 | 3/2008 | Higham | |
| 7,613,336 B2 | 11/2009 | Schultz | |
| 7,930,064 B2 | 4/2011 | Popovich, Jr. et al. | |
| 8,121,392 B2 | 2/2012 | Popovich, Jr. et al. | |
| 2002/0188466 A1 | 12/2002 | Barrette et al. | |
| 2004/0158350 A1 | 8/2004 | Ostergaard et al. | |
| 2006/0088196 A1 | 4/2006 | Popovich et al. | |
| 2006/0124656 A1 | 6/2006 | Popovich, Jr. | |
| 2007/0265880 A1* | 11/2007 | Bartfeld et al. | ............ 705/2 |
| 2008/0000979 A1 | 1/2008 | Poisner | |
| 2008/0119958 A1 | 5/2008 | Bear et al. | |
| 2008/0121000 A1 | 5/2008 | Vessa | |
| 2009/0012818 A1* | 1/2009 | Rodgers | ......... G01G 17/00 705/3 |
| 2009/0127339 A1 | 5/2009 | Needhan et al. | |
| 2010/0042395 A1 | 2/2010 | Rothschild | |

FOREIGN PATENT DOCUMENTS

| | | | | |
|---|---|---|---|---|
| WO | WO 00/06078 | | 2/2000 | |
| WO | WO 2008/137683 A1 | | 11/2008 | |
| WO | WO 2008137683 | * | 11/2008 | ......... G07F 11/58 |
| WO | WO2008137683 | * | 11/2008 | ......... G07F 11/58 |
| WO | WO 2009/058871 A | | 5/2009 | |

OTHER PUBLICATIONS

Jahr, I. "Chapter 3. Lighting in Machine Vision," Handbook of Machine Vision, Aug. 23, 2006, pp. 73-203.
PCT International Search Report and Written Opinion of the International Search Authority, PCT/US2011/027586, Jul. 18, 2011, 16 Pages.
European Supplementary Search Report, European Application No. 11753941.1, Sep. 13, 2013, 7 pages.
European Response to Search Opinion, Invitation under Rule 70a(2) EPC, European Application No. 11753941.1, Mar. 24, 2014, 7 pages.
Japanese Office Action, Japanese Application No. 2012-557174, Jan. 20, 2015, 2 pages.
Chinese First Office Action, Chinese Application No. 2011800220523, Feb. 3, 2015, 20 pages.
Chinese Second Office Action, Chinese Application No. 2011800220523, Sep. 14, 2015, 20 pages.
European Examination Report, European Application No. 11753941.1, Oct. 30, 2015, 7 pages.

* cited by examiner

MEDICATION VERIFICATION AND DISPENSING

CROSS REFERENCE TO RELATED APPLICATIONS

This application claims the benefit of U.S. Provisional Application No. 61/311,900, filed Mar. 9, 2010, which is incorporated by reference in its entirety for all purposes, including any appendices and attachments thereof.

BACKGROUND

This invention relates generally to an apparatus and method for verifying and dispensing medication.

Medication errors cause at least one death every day in the United States and injure approximately 1.3 million people annually. A Food and Drug Administration (FDA) study of fatal medication errors found that the most common errors involving medications were related to the administration of an improper dose of medicine (41%) and administration of the wrong medication (14%). Almost half of the fatal medication errors occurred in people over the age of 60, who often take multiple prescription medications. Such medication errors continue to occur despite federal regulations implemented in 1995 that require imprinting of identification codes on all medication solid oral-dosage forms.

The task of administering medications to a patient in a hospital or nursing home environment remains a manual process with limited quality assurance and that is highly subject to human error. Typically, a nurse reads a patient's prescription, opens a bottle of pills with the intended medication, places the pills in a small unlabeled plastic cup, carries the cup to the patient's bedside, and directs the patient to take the pills in the cup. There is no independent quality assurance process to confirm 1) that the correct medication and number of pills are placed in the plastic cup, 2) that the medications are delivered to the correct patient, or 3) that the medication is being administered at the correct time (e.g., not more than every 4 hours).

Patients in the home environment shoulder a substantial amount of responsibility in managing their own medications which can result in medication errors. Common errors in the home include taking the wrong dosage or quantity of pills, forgetting to take certain medications or doses, taking the medication at the wrong time, too many times a day, or not enough times a day, among other problems. For patients taking multiple medications a day or having medication regimes involving complex timing and administration factors, careful day-to-day management of their medications can become quite difficult.

Errors in medications can also arise in the pharmacy environment. Filled prescriptions can be mislabeled with the incorrect dosage or amount of pills, or with the incorrect medication. Pharmacists can dispense the wrong drug, quantity, or dosage, which are mistakes that can result in serious injury or even death of the patient. Pharmacists can make these types of mistakes as a result of being overworked or distracted, or even due to confusion between medication names that are similar, or pills that have similar physical appearances.

What is needed are an apparatus and method for verifying and/or dispensing medication in a manner that that identifies the medication and/or ensures the correct medication, dosage, and number of pills are provided to/taken by the proper individual at the appropriate administration time.

SUMMARY

Embodiments include a medication verification apparatus and method that is used (e.g. by a nurse, a pharmacist, a patient, etc.) to identify medications (e.g. any solid-dosage medications, such as pills, tablets, capsules, etc.) and/or ensure that the correct medications are taken by the correct person at the correct time. The apparatus takes images of the medication that can then be used to identify the medication and/or records characteristics of the medication. For example, the images can be compared to reference images to identify the medication, a signature of the image can be used to identify the medication, one or more characteristics of the medication can be used to identify the medication, among other mechanisms. The apparatus can further generate an indication of the identity of the medication.

According to some embodiments, the apparatus receives information about the individual to whom the medication will be administered (e.g., nurse/pharmacist enters patient name, scans a unique patient identifier, etc.), and the medication to be dispensed is placed into the apparatus or otherwise is in an area or compartment for analysis. In some embodiments, the apparatus further contains or accesses prescribing information for the patient and determines whether the medication is the correct medication(s), dosage strength, number, and time of day for the patient. The apparatus may then accept the correct medication for the patient and reject any medications that are not correct.

Embodiments include a medication dispensing apparatus and method. Medication (e.g., the medication accepted by the apparatus as a correct medication) can be dispensed into the dispensing portion of the apparatus. This dispensing apparatus includes a dispensing vessel that locks the medication inside. The dispensing vessel remains locked closed until it recognizes a unique identifier on or worn by the patient (e.g., on a patient wrist band). When it is confirmed that the patient is the correct patient, the dispensing vessel unlocks to allow the medication(s) inside to be administered to the patient.

Different embodiments of the medication verification apparatus may include various components. Some embodiments include a guide tube that receives the medication. Some embodiments include an identification component, such as an imaging device (e.g., one or more cameras) positioned adjacent to an imaging zone that takes images of the medication. Further embodiments include one or more sensors (e.g., one or more optical sensors, proximity sensors, etc.) positioned adjacent to a trigger zone of the guide tube records information about the pill as it passes through the guide tube (e.g., to set the proper timing or lighting for taking the image). Additional embodiments include a verification system that identifies the medication and an output system that generates an indication of the identified medication. In some embodiments, the verification system also compares the medication identified to the patient's prescription to verify that the medication is appropriate for the patient (e.g., is the correct medication, dosage, strength, timing, etc.). In some embodiments, a gating system in the apparatus accepts or rejects the medication based input from the verification system.

Different embodiments of the medication dispensing apparatus may include different elements. One embodiment includes a dispensing vessel having a closed body with an interior space, an opening for receiving the medication, and a lid covering the opening. An identification system on the dispensing vessel is programmable with an identification code for the patient to whom the medication is to be administered. A locking mechanism coupled to the lid locks the dispensing vessel to prevent access to the medication, but unlocks when the identification system recognizes a unique identifier for the correct patient.

In operation, the verification method can include various steps. One embodiment includes receiving a medication and taking an image of the medication. The method further includes identifying the medication and generating an indication of the medication identified. In some embodiments, the medication is compared to a prescription record of the patient to verify that the medication is appropriate for the patient, and is accepted or rejected based on the verification.

In operation, the dispensing method can also include a number of steps. One embodiment includes receiving a medication in a dispensing vessel and locking the medication inside the dispensing vessel. The method further includes reading a unique identifier for a patient (e.g., when the dispensing vessel is in proximity to the patient) and unlocking the dispensing vessel once the responsive to the unique identifier for the patient has been recognized.

BRIEF DESCRIPTION OF THE DRAWINGS

FIG. 5A illustrates an imaging zone in which the medication is static. FIG. 5B illustrates an imaging zone in which the medication is moving. FIG. 5C illustrates an imaging zone in which circumferential imaging devices take images of the medication. FIG. 5D illustrates an imaging zone in which mirrors are used to provide multiple perspectives of the medication with a single image.

FIG. 6A illustrates a gating system with a plunger air gate. FIG. 6B illustrates a gating system with a holding gate and an accept/reject gate.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Medication Verification and Dispensing Apparatus
Overview

Figure 1:
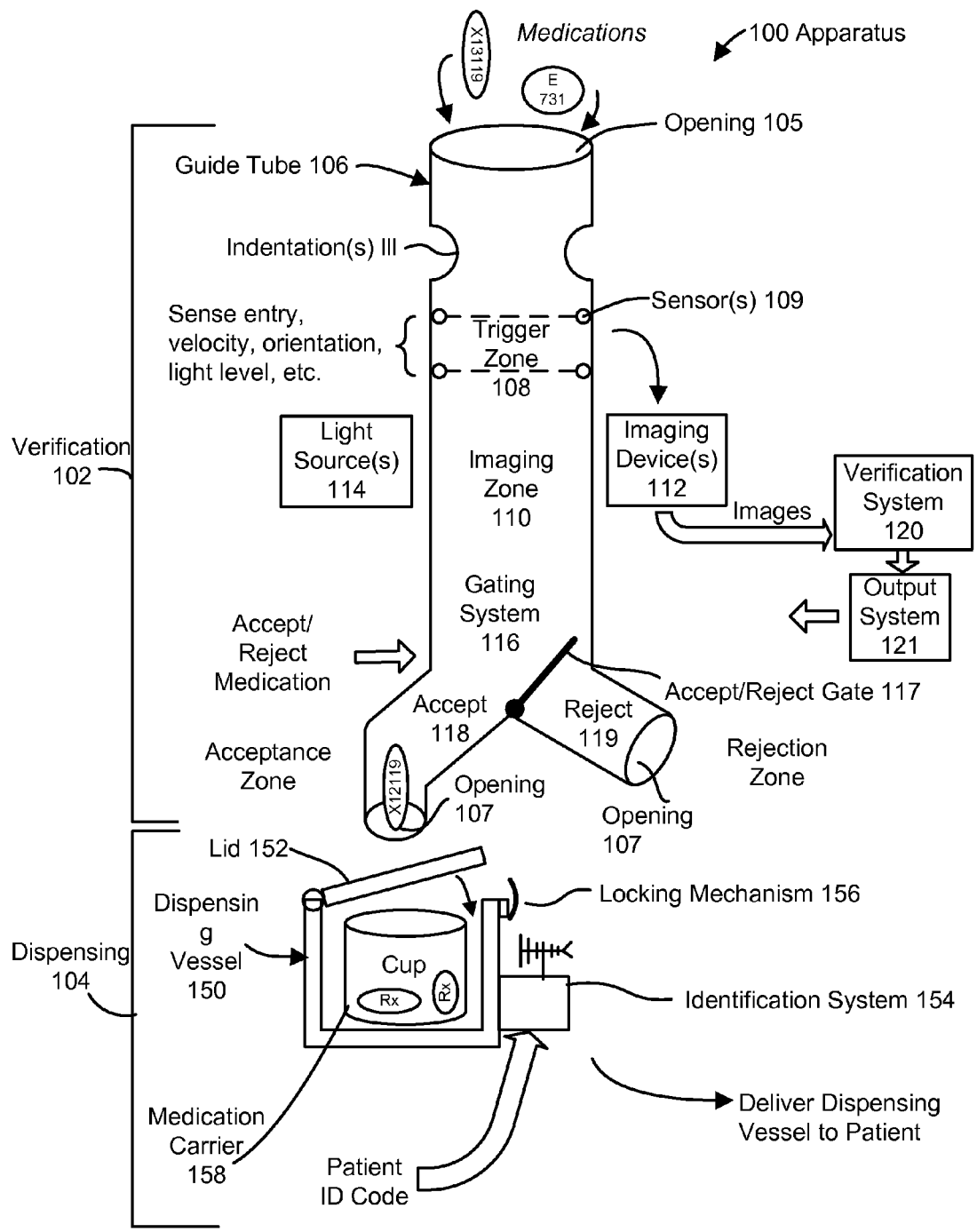
FIG. 1 illustrates a medication verification and dispensing apparatus, in accordance with an embodiment of the invention.

FIG. 1 illustrates a medication verification and dispensing apparatus 100, in accordance with an embodiment of the invention. A verification portion 102 of the apparatus 100 includes the guide tube 106, which can be any type of compartment or area, and various components associated with the guide tube 106. The dispensing portion 104 of the apparatus 100 includes the dispensing vessel 150 and its components.

The guide tube 106 or other compartment has a number of components in the embodiment illustrated in FIG. 1. The guide tube 106 includes an entry area on one end for receiving a medication and at least one exit area on another end for providing the medication. In one embodiment, the guide tube 106 includes an opening 105 on a first end which receives the medications. The medications to be analyzed are placed into the guide tube 106 through this opening 105. The guide tube also has at least one opening 107 on a second end for dispensing medication. In the embodiment illustrated in FIG. 1, the guide tube 106 has two openings 107, one for dispensing accepted medication and one through which rejected medications pass. The guide tube 106 further has a body between the openings 105, 107 that includes a passage through which the medication is delivered (e.g., a hollow tube). In addition, the guide tube 106 can have a lid or other covering for opening and closing the guide tube 106. The lid can be used to ensure that pills enter the guide tube 106 one at a time.

In one embodiment, the guide tube 106 includes indentations 111 or other types of uniform or non-uniform areas that the medication can contact and interact with while traveling through the passageway. These indentations 111 align or reorient the pill or cause the pill to rotate or move in a particular way. In this manner, the guide tube 106 can help to orient a medication so that images of the medication can be taken that allow the apparatus to identify the medication.

Some embodiments of the guide tube 106 include a trigger zone 108. One or more sensors 109 can be positioned adjacent to a trigger zone 108 for recording information about the pill as it passes through the guide tube 106. For example, these sensors 109 can set the proper timing for taking the image of the medication or for providing lighting during the taking of the image. The sensors 109 can sense entry of the medication into the trigger zone 108, velocity or orientation of the medication as it moves into or through the trigger zone 108, and the light level in the trigger zone 108, among other characteristics.

The guide tube 106 further includes an imaging zone 110 or an identification zone. One or more imaging devices 112 (e.g., cameras) or other identification components are positioned adjacent to the imaging zone 110 for taking one or more images of the medication within the imaging zone. In other embodiments, one or more identification components positioned adjacent to an identification zone for recording characteristics of the medication within the identification zone. The identification components can include imaging devices and sensors or other recording devices for recording physical or structural characteristics of the medication or of a marking on the medication. In some embodiments, the sensors 109 and imaging device(s) 112 are both identification components for receiving and/or recording characteristics about the medication. In addition, one or more light sources 114 can also be positioned adjacent to the imaging zone 110 for providing lighting or a flash for the images that are taken or for the recording of characteristics.

The image(s) taken and/or other characteristics recorded are then provided to or accessed by a verification system 120 that is in communication with the identification components or imaging device(s) 112. The verification system 120 identifies the medication based on the characteristics recorded (e.g., based on the image, based on a signature or fingerprint of the medication, based on structural or physical characteristics of the medication or markings on the medication, etc.). In one embodiment, the verification system 120 compares the image(s) of the medication to a collection of images of medications (e.g., reference images) in a database to identify the medication. In other embodiment, the verification system 120 uses one or more characteristics recorded for the medication to identify the medication (e.g., via optical character recognition, via analysis of structural/physical properties, via use of an image of the medication, etc. In addition, both comparison of images to a database and use of characteristics of the medication can be used to identifying the medication.

An output system 121 in communication with the verification system then generates an indication of the medication identified. For example, the output system 121 can display to a user of the apparatus 100 identifying information about the medication (e.g., name, dosage, etc.), can produce and save a file with identification information, or can otherwise notify the user about the identity of the medication.

In some embodiments, the indication of the medication identity is the output of the apparatus 100. In other embodiments, the apparatus further determines if the medication is correct for a particular patient, and accepts or rejects the medication accordingly. In these embodiments, the user of the apparatus 100 enters information into the apparatus 100 or otherwise provides an indication of the particular patient to whom the medication is to be administered. Once the verification system 120 has identified the particular medication in the guide tube 106 via imaging, the verification system 120 then compares the medication identified to a prescription record of a patient to verify that the medication is appropriate for the patient. For example, the verification system 120 can confirm whether the medication is a correct medication, strength, dosage, and/or amount to be administered to the patient, whether the current time (or an administration time entered by the user) is the correct time for administering that medication to the patient, and so forth. As used herein, the term "patient" refers to any individual taking a medication (including medications for home use), and the term includes both human and non-human or veterinary patients.

Some embodiments of the apparatus 100 include a gating system 116 that is mounted to or otherwise associated with the guide tube 106. The gating system 116 is positioned to accept or reject the medication based on input received from the verification system 120 indicating the medication identity or indicating whether or not the medication is appropriate for the patient. In some embodiments, the gating system includes an accept/reject gate 117 for routing the medication to different pathways in the guide tube based on whether the medication is accepted or rejected. For example, the accept/reject gate 117 is a swinging arm or door that moves to direct medication along two paths. The medication in FIG. 1 can be routed into the accept tube 118 or into the reject tube 119. If the medication is rejected, the medication should not be taken by the patient. If the medication is accepted, the medication will be dispensed from the apparatus 100 for administration to the patient.

While in some embodiments the user can immediately retrieve the medication from the verification portion 102 of the apparatus 100 following acceptance/rejection, in other embodiments a dispensing portion of the apparatus 104 restricts access to the medication once dispensed. This medication dispensing apparatus 104 can be used with the medication verification apparatus 102, or can be used independently for dispensing and transfer of medications. The medication dispensing apparatus 104 includes a dispensing vessel 150 having a closed body with an interior space and an opening through which medications can be received. A lid 152 covers the opening of the dispensing vessel 150. An identification system 154 (e.g., an RFID transceiver) is positioned on the dispensing vessel 150 and can be programmed with an identification code for a patient to whom the medication is to be administered. As used herein, the term "identification code" or "ID code" includes any code or identifier for uniquely recognizing a patient or distinguishing a patient from other patients.

A locking mechanism 156 is coupled to the lid 152 of the dispensing vessel 150 or otherwise associated with the dispensing vessel 150 for locking the dispensing vessel 150. The locking mechanism 156 unlocks the dispensing vessel to provide access to the medication when the identification system 154 recognizes a unique identifier for the patient. For example, where the identification system is an RFID transceiver, it recognizes an RFID tag worn by a patient when the transceiver is brought in proximity to the patient.

In some embodiments, the dispensing vessel 150 includes a medication carrier 158 or cup or bottle that holds the medications inside the dispensing vessel 150. The medication carrier 158 can be removable from the dispensing vessel 150. When the medications are to be administered or dispensed to a patient, the medication carrier 158 can be lifted from the dispensing vessel 150 and used to hold the medication for administration or delivery to the patient. The dispensing vessel 150 can then be returned to the apparatus 100 or otherwise put away for later dispensing. Where the dispensing vessel 150 is put back into the apparatus 100, the apparatus 100 can record the date and time the medications were administered to the patient. The medication carrier 158 can be washed and reused or can be a disposable holder. In some embodiments, to prevent the possibility of cross-contamination, the entire passageway of the guide tube 106 from the opening 105 in the apparatus to the medication carrier 158 in the dispensing vessel 150 is disposable. The apparatus 100 can be re-loaded with a new passageway/guide tube 106 and medication carrier 158 for each patient. Similarly, cross-contamination can be prevented with a sterile covering or lining inside the guide tube 106 which can be disposed of and replaced or washed and reused.

The apparatus 100 can be used in various environments, including in hospitals, nursing homes, in pharmacies, at home, in a research lab, and so forth. Where the apparatus is used in a hospital, nursing home, or similar medical environment, the apparatus functions in concert with the normal work flow of medical personnel administering medications to a patient. The medical personnel (e.g., doctors, nurses, technicians, hospital aides, etc.) are the users who use the apparatus 100 to verify and dispense medication for a patient. The medical personnel enter the name or other identifier for the patient into the apparatus, and the apparatus 100 ensures the correct medication, dosage, amount, etc. is dispensed for the correct patient at the correct time. The dispensing vessel 150 can be used to carry the dispensed medication to the appropriate patient in the hospital.

In a pharmacy, the apparatus 100 is used by the pharmacist, pharmacy technician, or other pharmacy personnel for dispensing solid-dosage medications to ensure that the correct medications are dispensed to the correct patient. The pharmacist enters into the apparatus the name or other identifier of a patient to be dispensed medications. The pharmacist can also enter the prescription information. The apparatus 100 contains or accesses the prescribing information for that patient. The pharmacist then places the medication to be dispensed into the apparatus 100. The apparatus 100 identifies the medication and checks the identity, dosage strength, and number against the patient's prescriptions. The system rejects any medications that are not correct based on the patient's prescription. The apparatus places the correct patient's medications into a pill bottle (e.g., the dispensing vessel 150). In some embodiments, the apparatus 100 secures a tamper proof cap onto the bottle and places a label onto the bottle containing the patient's name and prescription information.

In the home environment, the apparatus 100 is used by a patient to ensure that they are taking the correct medications at the correct time. In some embodiments, a portable, home-use version of the apparatus is used. The apparatus contains or accesses the prescribing information for that patient from the physician and/or pharmacy, and maintains a record of the date, time, medication and dosage previously taken by the patient. The patient can enter the prescription information directly. The patient places the medication to be taken into the apparatus. The apparatus 100 identifies the medication and checks the identity, dosage strength, number and time of day against up-to-date records of the patient's prescriptions and a record of previous medications taken by the patient. The apparatus 100 alerts the patient if any of the medications the patient places into the apparatus are not correct based on the patient's prescriptions and previous medications taken. After receiving confirmation that the medication is correct, the patient retrieves the medication from the apparatus 100 and takes the medication. In some embodiments, multiple dispensing vessels 150 can be used and set to open at specific days/times.

The apparatus 100 can further be used in a research environment. The apparatus logs the date/time a research medication is taken by a patient, and can track information about the medications administered over time. The apparatus 100 can further provide a dispensing log to a research sponsor providing data about the tracking of the research medication.

Figure 2:
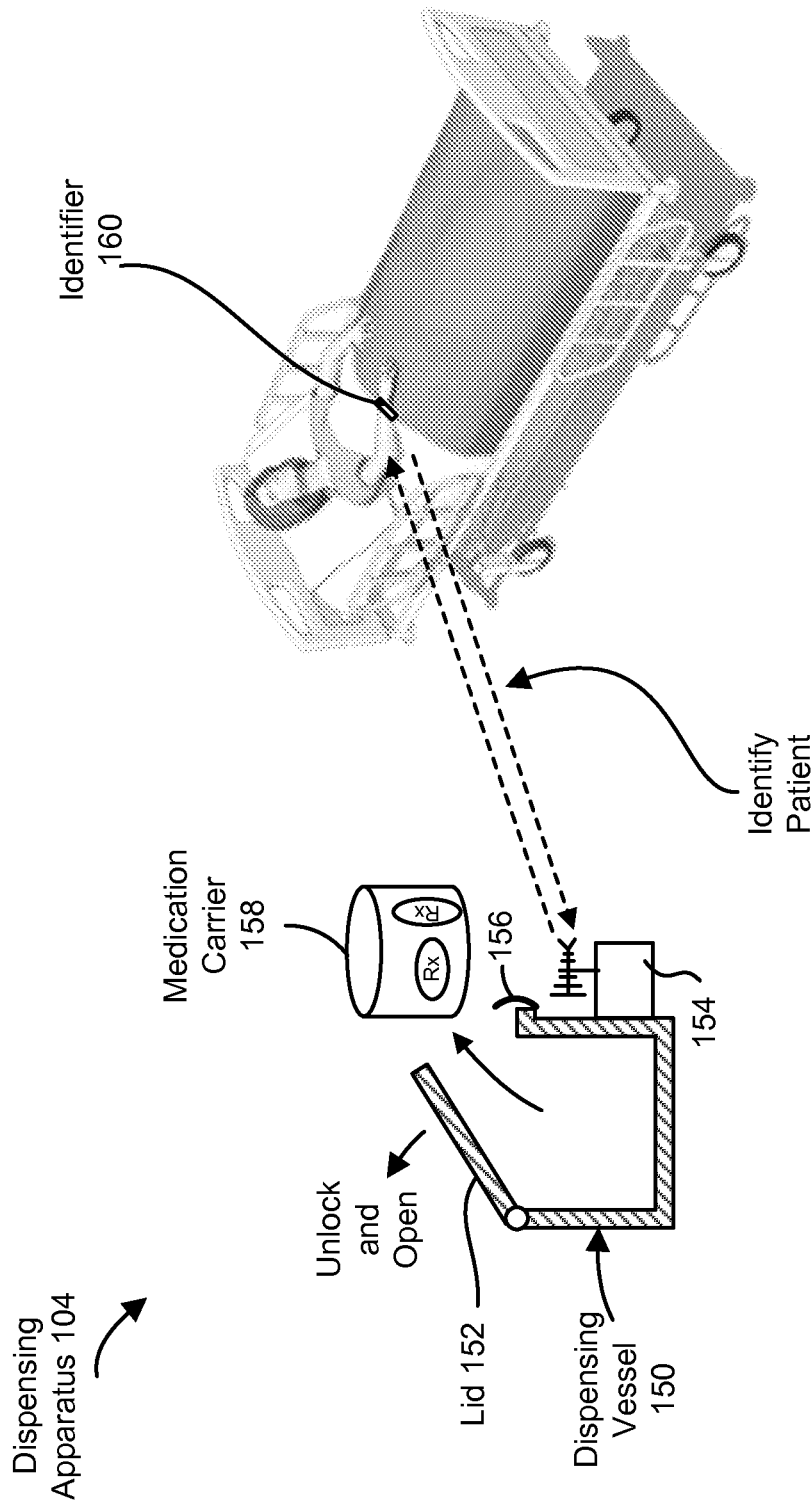
FIG. 2 illustrates a medication dispensing apparatus with a dispensing vessel unlocked upon recognition of the correct patient for a medication, in accordance with an embodiment of the invention.

FIG. 2 illustrates a medication dispensing apparatus 104 with the dispensing vessel 150 unlocked upon recognition of the correct patient for a medication, in accordance with an embodiment of the invention. The dispensing vessel 150 is a secured, locking enclosure that contains a patient's medications. In some embodiments, the medications are contained within a medication carrier 158 (e.g., a cup or bottle or holder) within the dispensing vessel 150. According to one embodiment, the dispensing vessel 150 has one or more sensors to confirm that the medication carrier 158 is loaded. The dispensing vessel 150 can hold one medication type or multiple medication types for a patient. Once the medication(s) are contained within the dispensing vessel 158, the sensor can detect that it is loaded and the locking mechanism 156 can lock the lid 152 of the dispensing vessel 150 closed.

As explained above, the dispensing vessel 150 can be used with the medication verification apparatus 102. In this case, the dispensing vessel 150 can fit into a slot or location in the apparatus 100 for holding the dispensing vessel 150. In some embodiments, the dispensing vessel 150 is locked or secured into the apparatus. A push button or other mechanism can be pressed or manipulated by the user to facilitate removal of dispensing vessel 150 from the apparatus. In some embodiments, a push button or other mechanism is also pressed/manipulated to remove the medication carrier 158 from the dispensing vessel 150. In some embodiments, the dispensing vessel 150 cannot be removed from the apparatus 100 until all of the medications for the patient to be taken at the current time are dispensed into the dispensing vessel 150.

The identification system 156 of the dispensing vessel 150 is programmed with the unique identification code for the patient. The dispensing vessel 150 can lock upon loading with medication or can lock upon removal from the apparatus 100. The identification system 156 can then be designed to allow the dispensing vessel 150 to unlock only upon identification of the correct patient for the medication. In some embodiments, the identification system 156 is an RFID transceiver or a barcode scanner (though other mechanisms can be used, as well) and is programmed with the unique identification code for the patient. The dispensing vessel is then taken from the apparatus and provided to the patient (e.g., delivered to the patient's hospital bedside). Each patient can wear or otherwise have an identifier 160 (e.g., on a wrist band or another item, such as on the patient's clothing, on a file kept with the patient, on the bed of the patient, etc.) containing a unique RFID tag, barcode, etc. When the dispensing vessel 150 is placed within close proximity to the patient's RFID wrist band or is used to scan a barcode on the identifier 160 (e.g., on a wrist band), it identifies the patient as the correct recipient of the medications and unlocks the dispensing vessel permitting removal of the medications. If the patient is not the correct recipient, the dispensing vessel 150 remains locked and the medications cannot be administered to the incorrect patient.

In one embodiment, the dispensing vessel 150 contains a clock and records the date and time the dispensing vessel 150 unlocks and medications are dispensed to the patient. The dispensing vessel 150 can further include a communication module that communicates the date and time of dispensing to apparatus 100 once the dispensing vessel 150 is returned to the apparatus 100 or remotely. In another embodiment, the dispensing vessel 150 sends a radio frequency signal to the apparatus 100 at the time of unlock and dispensing of medication to patient. In further embodiments, the dispensing vessel 150 and apparatus 100 communicate via Wi-Fi, BLUETOOTH®, etc. In a further embodiment, the apparatus 100 records the time and date that the dispensing vessel is removed from and/or replaced into the apparatus 100, and uses this to track medication administration.

Guide Tube

Figure 3:
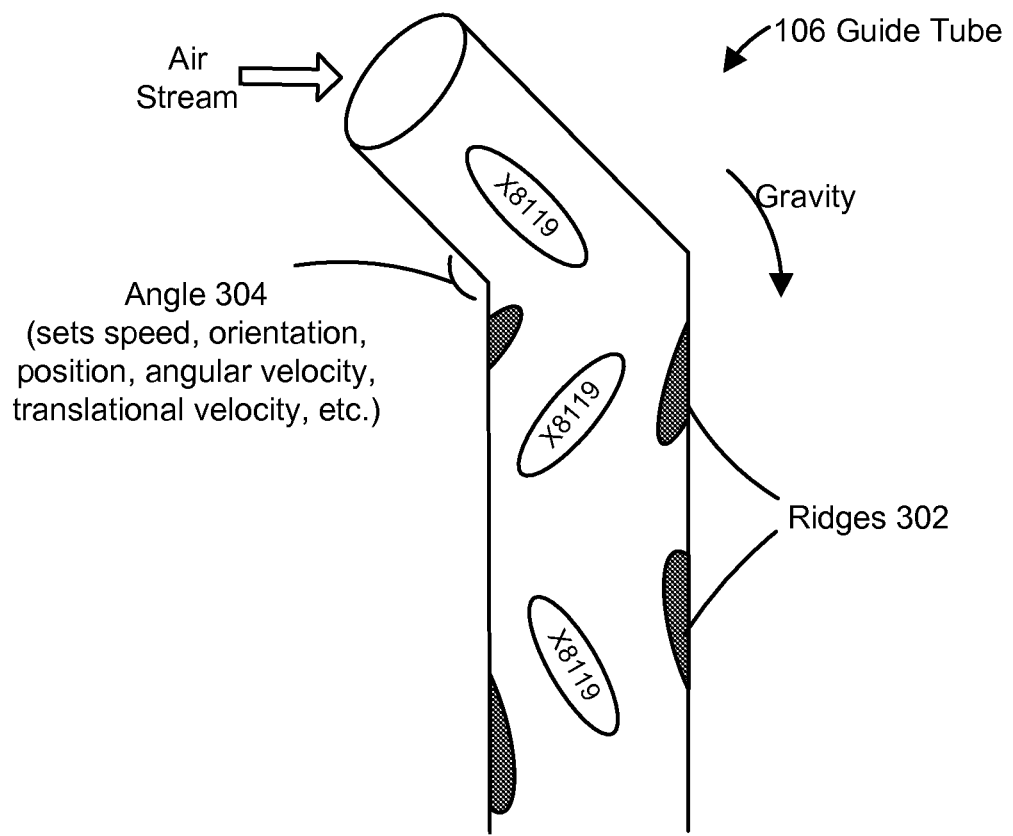
FIG. 3 illustrates a guide tube of a medication verification apparatus including various mechanisms for controlling orientation of the medication, in accordance with an embodiment of the invention.

FIG. 3 illustrates a guide tube 106 of a medication verification apparatus 102 including various mechanisms for controlling orientation of the medication, in accordance with an embodiment of the invention. The medication enters via an opening 105 in the guide tube 106 and passes through the guide tube 106 pulled by gravity propelled by a stream of gas, moving on a conveyor belt, or other such method for moving the medication. The guide tube 106 directs the medication to the imaging zone 110 in a manner to optimally orient the medication for identification. This may include various methods to control the orientation, position rotation, translational velocity, and angular velocity of each medication as it enters the imaging zone 110. Methods employed to control these factors may include the angle 304 of approach of the medication to the imaging zone and/or ridges 302 or indentations 111 in the guide tube 106 to position or induce tumbling of the medication.

The shape of the guide tube 106, the orientation of the guide tube 106 to the force of gravity or other source of force, and the coefficients of friction and drag can be specifically designed to orient the axis of each pill in the direction of travel or with the axis of the tube 106. This orients the flat or partially curved surface of the pill parallel to or orthogonal to one or more of the imaging devices 112 and minimizes tumbling or rolling of the pill. The shape and optical properties of the guide tube 106 in the imaging zone 110 are designed to permit overlapping or continuous fields of view of the pill by each of the imaging devices 112. Further, this minimizes internal and external reflections from emitted sources (e.g. light) and minimizes reflections and distortion of the emission or transmissions coming from each pill. The forces that impart movement, orientation, position, translational velocity, and angular velocity are provided in part or completely by gravity, friction, a mechanical device (e.g., a vibration device, a conveyor belt, a plunger, etc.), or gaseous system (e.g., air, nitrogen, CO2, etc)).

The guide tube 106 may have various different shapes. In one embodiment, the guide tube 106 is circular or semicircular. In another embodiment, the guide tube 106 is flat or partially curved on one or more surfaces. In a further embodiment, the cross-section of the guide tube 106 is square, pentagonal or is a polygon of n-sides. In an additional embodiment, the guide tube is open along its length or is a guide platform on which the medication rests or is moved. In a further embodiment, the guide tube 106 is any type of area or compartment. In another embodiment, the guide tube is not included in the apparatus 100, and the image is taken in an imaging or characteristic recording area.

Where the guide tube 106 has the shape of a polygon, a camera and lighting apparatus can be positioned above each face of the guide tube polygon in the imaging zone 110. In another embodiment, a camera and lighting apparatus are positioned in the imaging zone 110 above each flattened surface of the pill and circumferentially around the pill. In a further embodiment, the guide tube 106 is discontinuous in the imaging zone 110 after having imparted the desired orientation, position, translational velocity, and angular velocity to the pill.

The internal surface of the guide tube 106 can vary for different designs. In one embodiment, the internal surface of the guide tube 106 is smooth. In another implementation, the internal surface of the guide tube 106 has ridges (e.g., ridges 302), grooves, bumps, and/or discontinuities that impart the desired orientation, position, translational velocity, and angular velocity to the pill. The coefficients of friction, static and dynamic, between the guide tube 106 and the pill are controlled by the composition of the guide tube 106, and/or by coatings, materials, or treatment of the surface of the guide tube 106 that comes in contact with the pill. The coefficients of friction are engineered in such a manner to provide for the desired orientation, position, translational velocity, and angular velocity of pills of various compositions of matter.

The user may or may not assist in ensuring the optimal orientation of the pill for imaging. In one embodiment, the user imparts an initial orientation, position, translational velocity, and angular velocity to the pill upon placement into the guide tube 106. In another embodiment, the pills enter the guide tube 106 with random orientation, position, translational velocity, and angular velocity.

The guide tube 106 can be made from various materials. In one embodiment, the guide tube 106 is made of glass, plastic (e.g. acrylic or polycarbonate) or another low-distortion transparent material. The guide tube 106 may be transparent in its entirety or just in the imaging zone. The guide tube 106 may further have the same shape throughout or may have one or more different shapes in different regions.

The orientation of the guide tube can vary with different implementations. In one embodiment, the guide tube is oriented approximately 5 to 89 degrees to the force of gravity or other external force exerted on the pill. In another embodiment, the net force of a gas or mechanical device or vibration acts in the direction of travel along the long axis of the tube or in the direction of travel of the pill.

Trigger Zone

Figure 4:
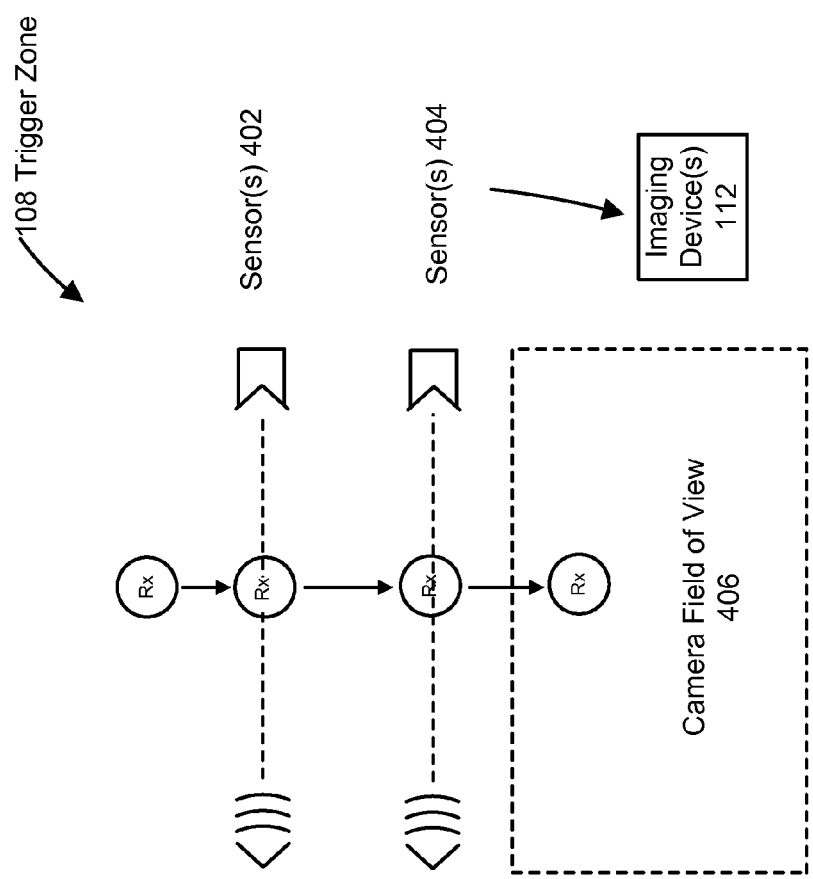
FIG. 4 illustrates a trigger zone of a guide tube in a medication verification apparatus, in accordance with an embodiment of the invention.

FIG. 4 illustrates a trigger zone 108 of a guide tube 106 of a medication verification apparatus 102, in accordance with an embodiment of the invention. This region can include a system to set the proper timing for the imaging device 112 and lighting 114 in the imaging zone 110. This may entail passing through an optical sensor (e.g. a laser) or other such proximity sensor to detect the presence of a medication and to determine the velocity, orientation, etc. of the medication as it enters the imaging zone 110. For example, the sensors can set the proper timing for taking the image of the medication or for providing lighting during the taking of the image. The sensors can sense entry of the medication into the trigger zone 108, velocity or orientation of the medication as it moves into or through the trigger zone 108, the light level in the trigger zone 108, among other characteristics. The sensors can be limited to one area of the guide tube 106 (e.g., the trigger zone 108) or can be included in multiple areas or throughout the guide tube 106.

The embodiment of FIG. 1 includes two sensors 402 and 404. FIG. 1 illustrates the medication as it passes through the trigger zone 108 past each of sensors 402 and 404, and then into the field of view 406 for the imaging device 112. The trigger zone 108 can include only one sensor or many sensors. The sensors can be of the same type or of various different types. For example, sensor 402 could be a laser or a light sensor, and sensor 404 could be a sensor that detects velocity, origination or timing of the medication as it passes by.

Imaging Zone

FIGS. 5A-5D illustrate an imaging zone 110 of a guide tube 106 of a medication verification apparatus 102, in accordance with an embodiment of the invention. The imaging zone 110 includes one or more imaging devices 112 and a lighting system 114 capable of obtaining high resolution, macroscopic images of each medication that are of sufficient quality and number to be used to uniquely identify each medication. The imaging device 112 may include one or more high speed video cameras and/or one or more stationary cameras that collect images of each medication as it passes through the imaging zone 110. Types of imaging devices can further include optical area, optical line scan, infrared area, infrared line scan, x-ray, etc. The lighting system 114 may include one or more strobe light sources, one or more fixed light sources, among others. The position of the light source(s) 114 with respect to the camera(s) 112, and with respect to the medication, is such that the optical contrast is sufficient to image embossed, debossed, or engraved imprints on the medication surface.

Figures 5A, 5B:
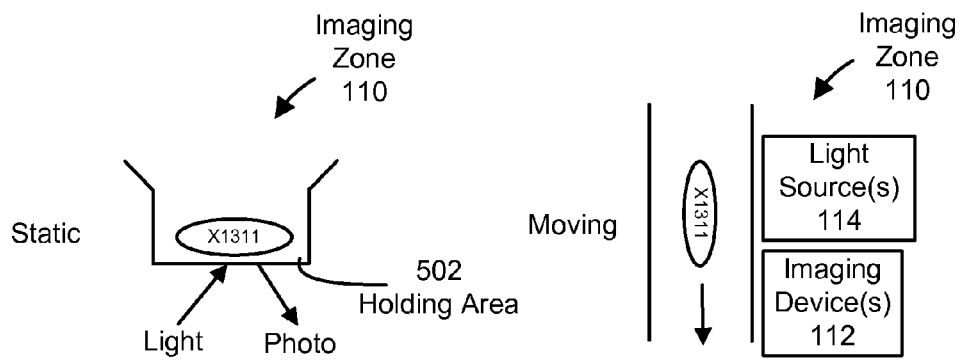
FIGS. 5A-5D illustrate an imaging zone of a guide tube in a medication verification apparatus, in accordance with an embodiment of the invention.

FIG. 5A illustrates an imaging zone 110 in which the medication is static and FIG. 5B illustrates an imaging zone 110 in which the medication is moving. In the FIG. 5A embodiment, the pills remain stationary while the imaging device 112 takes the image. This can be accomplished by having a holding area 502 or trap door that holds the medication in place while the imaging device 112 takes the picture and then releases the pill to continue its travel through the guide tube 106. In the FIG. 5B embodiment, the imaging device 112 snaps the picture of the medication as it moves through the guide tube 106. The guide tube 106 can also be angled so the medication slides along a surface of the tube 106 while the image is taken.

Figure 5C:
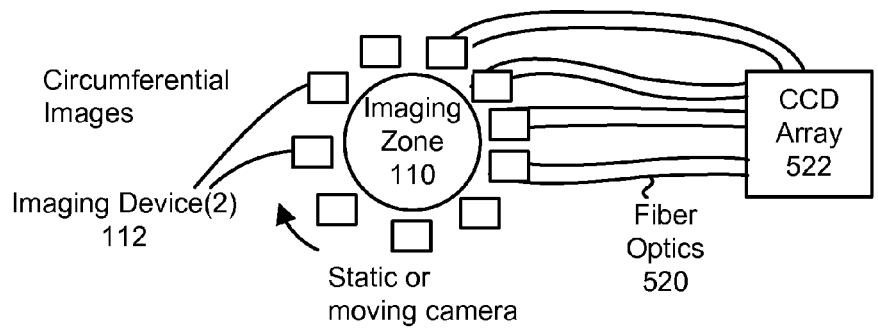

FIG. 5C illustrates an imaging zone 110 in which circumferential imaging devices 112 take images of the medication. The imaging device 112 may further include a movable camera or scanning array with a fixed and/or movable lighting system that takes peripheral photographs or video images as the imaging device 112 rotates around the stationary or moving medication. Thus, the camera(s) and light source(s) move around the pill, while the pill is stationary or moving. In another embodiment, the medication is made to rotate as a peripheral image is collected by a stationary camera or video system. Cameras with fast shutters may be used with continuous light sources to minimize the motion of the pill in the image. In addition, the light sources may be strobe lights, and the cameras may have fast or slow shutter speeds to minimize the motion of the pill in the image. In the embodiment of FIG. 5C, the imaging devices 112 are connected via fiber optic cables 520 or other cables to a charge-coupled device (CCD) array 522.

Figure 5D:
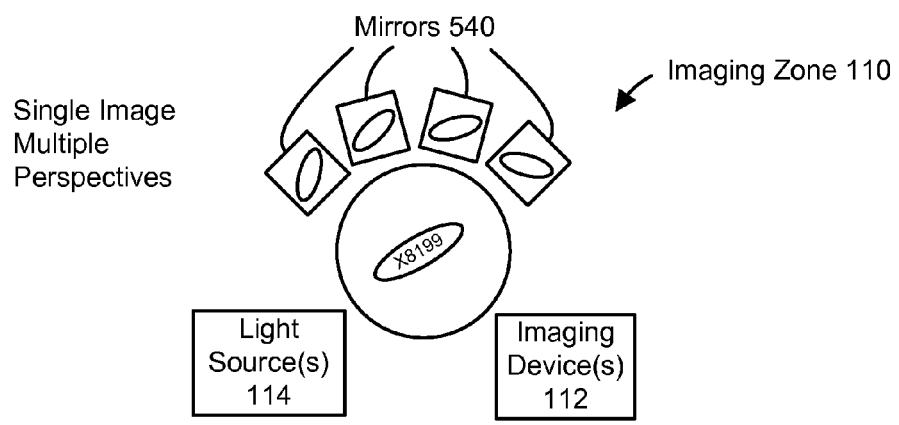

FIG. 5D illustrates an imaging zone in which mirrors are used to provide multiple perspectives of the medication (e.g., with a single image). Thus, the imaging device 112 can be positioned in one location, and the mirrors can be placed in various positions around the medication so that multiple angles can be captured. In some embodiments, the mirrors are automatically adjustable and can move to capture the best image of the pill depending on how the pill is oriented when it is in the imaging zone 110. Further, multiple cameras in different orientations and/or mirrors 540 may be used to obtain images of different sides and/or perspectives of the medications.

Control of the light sources 114 is coordinated with the exposure of each imaging device 112 such that the pill is optimally illuminated for that particular imaging device 112. The timing of the light sources 114 is coordinated to minimize direct and/or back lighting of the pill during the exposure of each imaging device 112. The position and orientation of the imaging devices 112, the position and orientation of the lighting 114, the timing of the lighting 114, the timing of exposure and the duration of exposure, etc. are designed and coordinated to minimize motion artifacts, minimize reflections and distortion from the guide tube 106, and provide for the collection of a plurality of images sufficient to uniquely identify each pill.

Solid dosage forms of medications contain unique identification codes. These imprinted identification codes can be embossed, debossed, engraved or printed on the medication. Trademark letters, marks, symbols, internal and external cut outs are also commonly present on the surface of solid dosage forms of medications. Additional features that aid in the unique identification of medications include shape, color, size, and scoring.

Direct or bright field illumination, while good for imaging printed markings, is poorly suited to imaging of embossed, debossed, or engraved imprints. Tangential, (dark field, off-axis) illumination enhances the contrast of surface features, at the expense of illuminating flush printed markings.

Illumination of the pills is accomplished by one or more light sources 114 designed and positioned to provide high-contrast illumination of embossed, debossed, and/or engraved features, as well as printed markings on the surface and color, shape, and size. To accomplish this, lights 114 are positioned surrounding each camera's field of view, with their incident light path raised or recessed and at an acute angle with respect to the plane containing the pill being imaged.

Light sources 114 are positioned such that a greater proportion the incident light is reflected off the indented and/or raised edges of embossed/debossed markings towards the camera then the light reflected off the pill surface and/or the light reflected off the valleys and/or peaks of the embossed/debossed markings. One or more light sources 114 are used to illuminate the various edges of the embossed/debossed markings oriented at different angles to the light path of each light source 114 and to the camera 112. The net effect of the lighting pattern is to illuminate each pill in such a way that the features of the debossed, embossed, and engraved imprints are prominent, distinguishable and uniquely identifiable.

The light sources 114 can be positioned in various manners. In one embodiment, the pill is illuminated by 1) a plurality of light sources above and below the pill, raised or in the plane of the pill and projecting at an acute angle of incidence to the plane of the pill, and/or 2) a plurality of light sources on the sides of the pill, raised or in the plane of the pill and projecting at an acute angle of incidence to the pill. In one embodiment, the light sources are continuous. Continuous light sources include tungsten, halogen, fluorescent, or incandescent light sources. In another embodiment, the light source is a high-speed strobe. Strobe lights can be flash tube, tungsten, halogen, xenon, or LED lights. In a further embodiment, the light source 114 is a combination of continuous and strobe lights. In an additional embodiment, the light sources 114 are infrared, ultraviolet, and/or x-ray light sources.

Various optical devices can also be used in the imaging zone 110. In one embodiment, optics are placed in line with the light source. The optics can focus the light sources on the pill, and may contain diffuser elements and/or a collimator. In one embodiment, the optics have narrow or broad illumination patterns. In another embodiment, the optics have spherical, elliptical or other such shaped illumination patterns.

A variety of different imaging devices can be used. In addition, to those described above, the imaging can be done using light reflection, light absorption, fluorescence, magnetic resonance imaging, x-ray imaging, x-ray diffraction, infrared, ultraviolet, line scan, refractive index, among others.

Other identification mechanisms can be used as well, including various chemical analysis methods. For example, the medication can be identified using spectroscopy, smell, weight, chromatography, etc. The medication can be identified using one or more electrochemical properties, such as conductivity, resistance, inductance, impedance, Cyclic Voltammetry, etc. The medication can further be identified using electrophoresis (e.g., capillary), volumetric analysis, weight, density, etc.

The medication can also be identified using various spectroscopy methods. For example, the spectroscopy methods can include atomic absorption or fluorescence, atomic emission, ultraviolet, visible, x-ray, alpha particle, fluorescence, infrared, Raman, nuclear magnetic resonance, photoemission, mass, energy dispersive, Fourier transform, laser-induced breakdown, particle-induced s-ray emission, s-ray fluorescence, Auger electron, appearance potential, angle resolved or angle resolved ultraviolet photoemission, coaxial impact collision ion scattering, coherent anti-stokes Raman, correlation, dielectric, deep-level transient, differential reflectance, exclusive correlation, energy Dispersive, Energy dispersive x-ray, electron energy loss, electron, electron spin resonance, exchange, fluorescence correlation, fluorescence cross-correlation, Fourier transform infrared, high resolution electron energy loss, ion induced auger electron spectroscopy, inductively coupled plasma atomic emission, inelastic electron tunneling, ion scattering, laser induced breakdown, laser optical emission, Mössbauer, nuclear Overhauser effect, optical emission, positron annihilation, photoacoustic, potentiodynamic electrochemical impedance, photocurrent, photothermal deflection, parallel electron energy loss, photoelectron, photothermal, reflectance Difference, resonance Raman, surface enhanced infrared absorption, surface enhanced Raman or resonance Raman, Stark spectroscopy, scanning tunneling, UV-photoelectron, ultrasound attenuation, x-ray induced Auger electron spectroscopy, wavelength dispersive x-ray, particle (or proton) induced gamma-ray or x-ray, sputtered neutral species mass, electron paramagnetic resonance, glow discharge optical, ion neutralization, and x-ray photoelectron spectroscopy.

In addition, spectrometry methods can be used for identification. The spectrometry methods can include elastic (non-Rutherford) backscattering, electrospray ionization mass or electrospray mass, forward recoil, Fourier transform ion cyclotron resonance or Fourier transform mass, glow discharge mass, inductively coupled plasma mass liquid chromatography-mass, mass, tandem mass, Rutherford backscattering, secondary ion mass, selected-reaction-monitoring capillary-electrophoresis mass, and time-of-flight mass spectrometry.

Furthermore, microscopy methods can be used for identification. The microscopy methods can include optical, electron, scanning probe, x-ray, scanning electron, scanning x-ray, scanning transmission x-ray, transmission electron, atomic force, atom probe field ion, charge collection, confocal laser scanning, cryo-electron, differential interference contrast, energy filtered transmission electron, environmental scanning electron, electrochemical scanning tunneling, field emission, focused ion beam, field ion-atom probe, fluorescence, high-resolution electron, high-resolution transmission electron, intermediate voltage electron, low-energy electron, magnetic force, multiphoton fluorescence, magnetic resonance force, Nanovid, near-field optical, phase contrast, photon-induced near-field electron, reflection electron, scanning Auger, Scanning confocal electron, scanning ion-conductance, scanning near-field optical, scanning probe, scanning electron or transmission electron, scanning tunneling, transmission electron, total internal reflection fluorescence, x-ray photoelectron emission, stimulated emission depletion microscopy, two-photon excitation, and video-enhanced differential interference contrast microscopy.

Various chromatography methods can be used in identification, such as gas chromatography, gas chromatography-mass spectrometry, gas chromatography-IR spectroscopy, gel permeation chromatography-IR spectroscopy (GPC-IR), high performance liquid chromatography, size exclusion, liquid chromatography-IR, liquid chromatography-mass, pyrolysis gas chromatography, and gas-liquid chromatography. Various tomography methods can be used too, such as cryo-electron tomography, electrical capacitance tomography, electrical impedance or electrical resistivity tomography, magnetic induction tomography, photoacoustic or photoacoustic computed tomography, single photon emission computed tomography, and thermoacoustic or thermoacoustic computed tomography.

In addition to all of these identification methods, the medication can be identified using colorimetry, differential scanning calorimetry, dual polarisation interferometry, resonance (e.g., nuclear magnetic resonance, magnetic resonance imaging, electron paramagnetic, electron spin, etc.), field flow fractionation, flow injection analysis, ion microprobe, inductively coupled plasma, ion selective electrode (e.g. determination of pH), neutron activation analysis, resonance enhanced multiphoton ionization, μSR (e.g., Muon spin spectroscopy, $\chi$ (e.g., magnetic susceptibility). The medication can further be identified using analytical ultracentrifugation, auger electron diffraction, attenuated total reflectance, BET surface area measurement (from Brunauer (Emmett (Teller)), bimolecular fluorescence complementation, backscatter Kikuchi diffraction, bioluminescence resonance energy transfer, back scattered electron diffraction, convergent beam electron diffraction, coherent diffraction imaging, capillary electrophoresis, cathodoluminescence, cyclic voltammetry, dielectric thermal analysis, De Haas-van Alphen effect, dynamic light scattering, dynamic mechanical analysis, differential scanning calorimetry, differential thermal analysis, dynamic vapour sorption, electron beam induced current (ion beam induced charge), electron backscatter diffraction, energy-dispersive analysis of x-rays, electrically detected magnetic resonance, electron induced desorption, electroluminescence, electron crystallography, electrophoretic light scattering, electron nuclear double resonance, electron probe microanalysis, elastic recoil detection or Elastic recoil detection analysis, electron stimulated desorption, extended x-ray absorption fine structure.

The medication can further be identified using mechanisms such as flow birefringence, fluorescence anisotropy, fluorescence lifetime imaging, fluorescence resonance energy transfer, grazing incidence small angle x-ray scattering, grazing incidence X-ray diffraction or reflectivity, high angle annular dark-field imaging, helium atom scattering, ion beam analysis, immunofluorescence, ion cyclotron resonance, intelligent gravimetric analysis, ion induced x-ray analysis, isothermal titration calorimetry, low-angle laser light scattering, low-energy electron diffraction, low-energy ion scattering, light scattering, matrix-assisted laser desorption/ionization, molecular beam epitaxy, medium energy ion scattering, magnetic resonance imaging, microthermal analysis, neutron activation analysis, neutron diffraction, neutron depth profiling, near edge X-ray absorption fine structure, nuclear inelastic scattering/absorption, nuclear reaction analysis, optical beam induced current, optically detected magnetic resonance, osmometry, photoemission of adsorbed xenon, photoelectron diffraction, photodesorption, photoelectron diffraction, photoluminescence, porosimetry, powder diffraction, quasi-elastic neutron scattering, resonant anomalous x-ray scattering, reflection high energy electron diffraction, resonant inelastic x-ray scattering, selected area electron diffraction, small angle neutron scattering, small angle x-ray scattering, surface composition by analysis of neutral species and ion-impact radiation, spectroscopic ellipsometry, surface extended X-ray absorption fine structure, solid immersion lens, solid immersion mirror, solid-state nuclear magnetic resonance, surface x-ray diffraction, thermogravimetric analysis, transmitting ion kinetic analysis, thermomechanical analysis, total reflection x-ray fluorescence analysis, ultrasonic testing, voltammetry, wide angle x-ray scattering, x-ray crystal truncation rod scattering, x-ray crystallography, x-ray diffuse scattering, x-ray diffraction, x-ray resonant exchange scattering, x-ray fluorescence analysis, x-ray reflectivity, x-ray Raman scattering, and x-ray standing wave technique.

Gating System

Figure 6A:
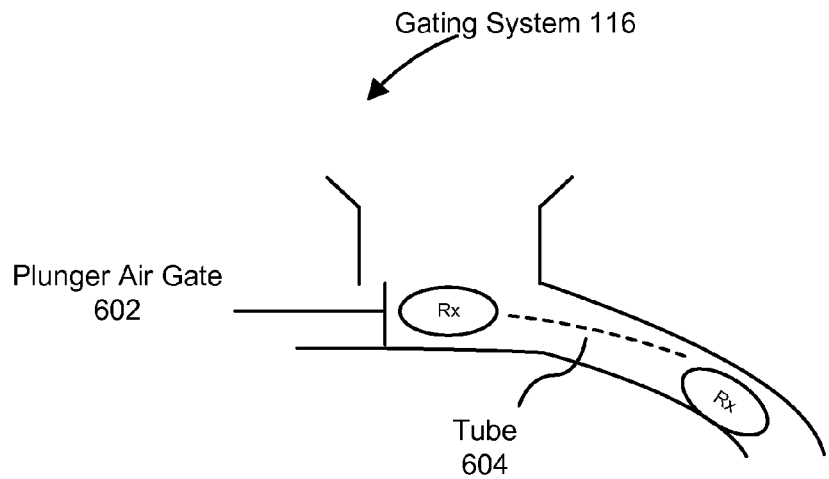
FIGS. 6A-6B illustrate a gating system of a guide tube in a medication verification apparatus, in accordance with an embodiment of the invention.
Figure 6B:
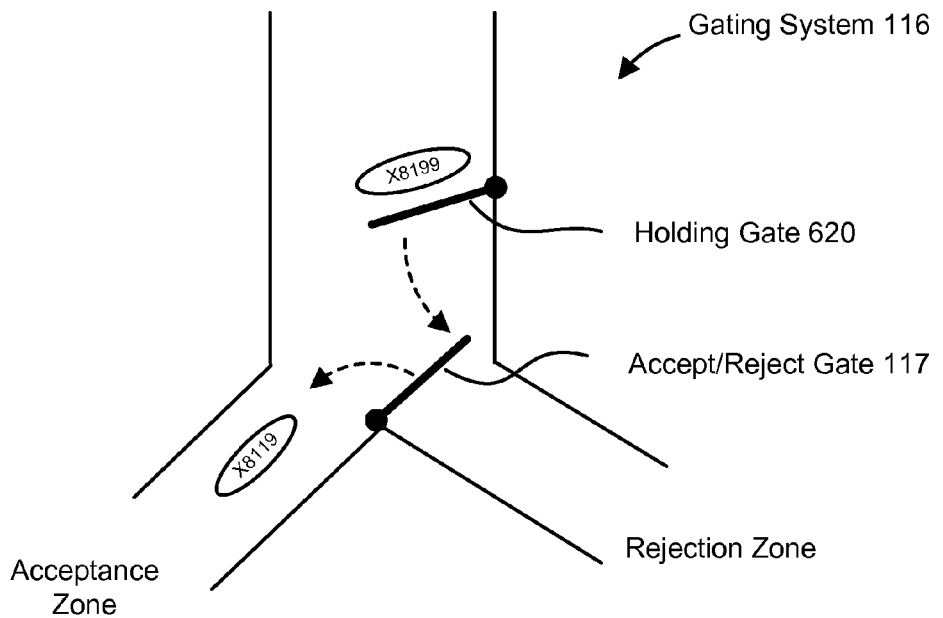

FIGS. 6A-6B illustrate a gating system 116 of a guide tube 106 in a medication verification apparatus 102, in accordance with an embodiment of the invention. The gating system 116 may be placed after the imaging zone 110 to direct the medication either into the dispensing vessel 150, or to a rejection zone. The gating system 116 receives input from the verification system to accept or reject each medication. In one embodiment, the gating system 116 includes a holding area and a system to direct, move or otherwise change the direction of movement of the medication through the system. The direction and movement of the medication is controlled by gates, doors, openings, plungers, conveyors, gas or a combination thereof.

The system rejects any medications that are not correct based on the patient's prescriptions, the time of day, or previous medications administered to the patient. In the event that an incorrect medication (e.g. type, number, time of day, etc.) is placed into the apparatus 100, the system signals an error alert or otherwise notifies the user and rejects the medication. In this case, the dispensing vessel 106 is not programmed with the patient's identification code and does not permit the medication to be administered to the patient. Medications determined to be incorrect for the patient can be directed to the rejection zone. The rejection zone provides for retrieval of incorrect medications that can then be restocked. In some embodiments, there is no separate tube or rejection zone. Instead the medication can be dispensed into the dispensing vessel 150, but the apparatus 100 can warn the user and refuse to release the dispensing vessel 150 with the rejected medication inside.

FIG. 6A illustrates a gating system with a plunger air gate 602. The plunger design can push the medication to direct it into a tube 604, such as an acceptance or rejection tube. FIG. 6B illustrates a gating system with a holding gate 620 and an accept/reject gate 117. The holding gate 620 can be used to catch the pill and hold it until the verification system has indicated whether it should be accepted or rejected. The accept/reject gate 117 can then move accordingly, depending on whether the pill should be accepted or rejected. The holding gate 620 can then release the pill, which can slide along the accept/reject gate and into the tube for acceptance or for rejection.

Verification System

Figure 7:
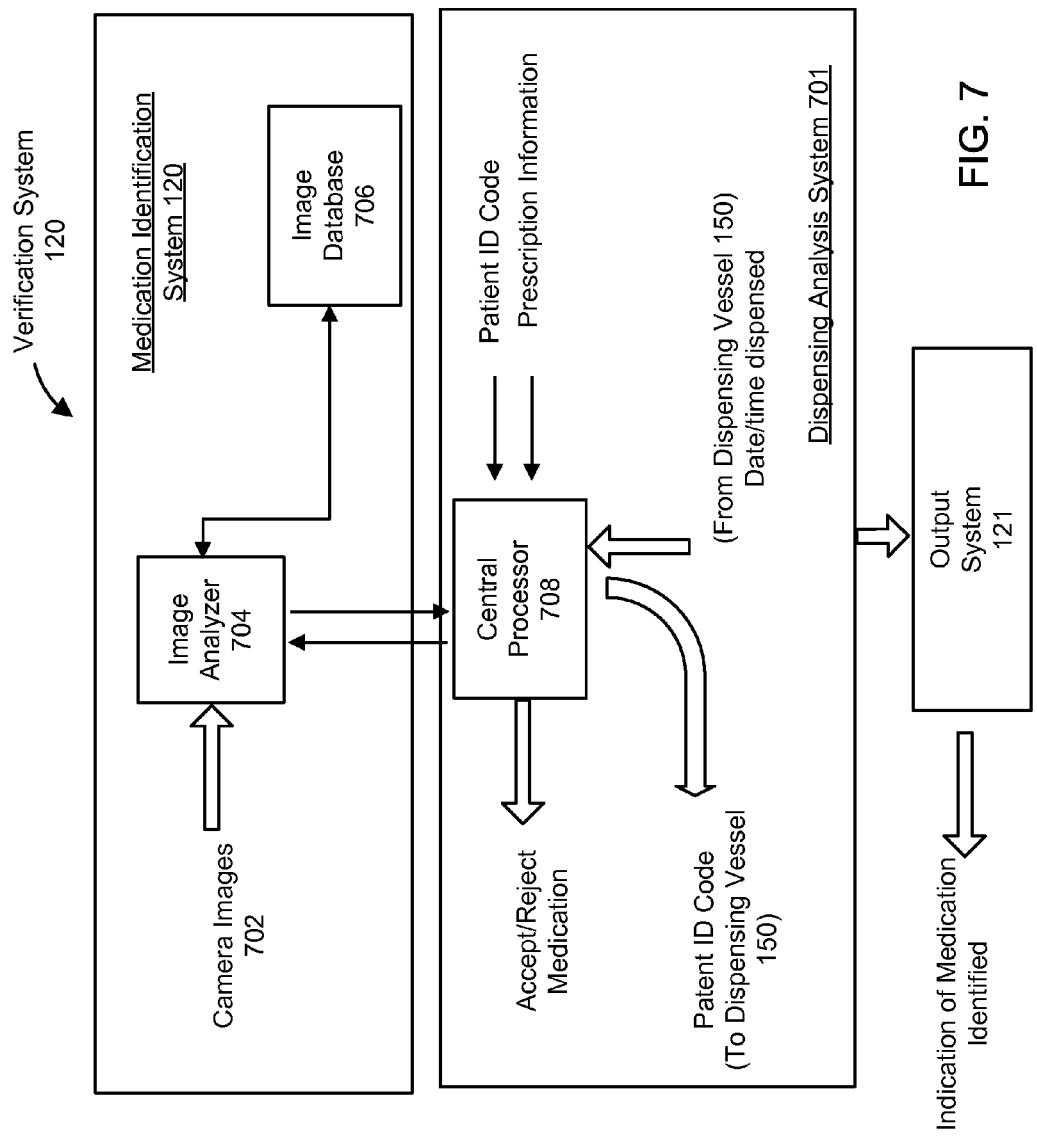
FIG. 7 illustrates a verification system including a medication identification system and a dispensing analysis system, in accordance with an embodiment of the invention.

FIG. 7 illustrates a verification system 120, in accordance with an embodiment of the invention. In one embodiment, the verification system 120 includes two components: a medication identification system 700 and a dispensing analysis system 701. System 700 includes an image analyzer 704 and includes or has access to an image database 706. The medication identification system 700 receives or accesses the images taken by one or more imaging devices 112. The images are then compared against the database 706 of reference images for various medications. Images of each medication can be analyzed in a manner to uniquely identify the medication as being one from the list of medications prescribed to the patient.

The methods for medication identification may include 1) optical recognition of characters embossed, debossed, engraved or printed on the medication, 2) optical recognition of identifying markings, such as trademark letters, marks, symbols, internal and external cut outs, 3) comparison of medication images, characters and markings to a database containing known medication images, characters and markings, 4) analysis of the medications structural properties (e.g. shape, color, size, scoring), and 5) analysis of medication physical properties (e.g. weight, density). Analysis of medication images may include 1) methods to rotate and/or warp of the images, 2) combining or analyzing different portions of the same image (e.g. mirror showing side, back views), and 3) combining or analyzing separate images (e.g. images from different orientations or perspectives, images extracted from video sequence).

In some embodiments, the identification system 700 identifies the medication based on a signature of the image of the medication, where the signature is a measurement of the properties of a medication. The signature can include a color, a pattern, a shape, a size, a texture, a mass, a weight, or a volume of a medication. The signature can also include a font, a color, a size, or a type of a symbol or character on a medication. The signature or characteristics recorded about a medication can include, but are not limited to, the color or coloration pattern (e.g., sky-blue pill, purple pill with black stripe and red lettering, white pill with symbols on one side only, etc), the symbols or characters on a medication (e.g., by optical character recognition, symbol recognition, image-pattern analysis, etc) as well as their location (e.g., in the center, near another symbol, near a corner, line, edge, or other recognizable second feature), volume, shape (e.g., round, triangular, tablet or capsule), size, shading, color or texture (e.g., containing grains or uniform composition), font, font color, font size, or other distinguishing features of symbols recognized on the medication. Features such as mass, weight, volume, dimensional measurements, or other readily-imaged or recorded physical properties of a medication can also be included. Individual signatures can further be combined to create a new signature that better identifies a medication (e.g., purple pill with black stripe 25% distant from one end, flanked by white lettering, etc.).

Where the signature is compared to a database, it can be compared to a database in many ways. In some embodiments, comparing a signature to a database includes identifying a match to one or more of a known list of targets, such as a list of known pharmaceuticals, or a list of known pills. For example, a signature can be a match lookup in a table, list, hash, or other comparison by equality or similarity according to a formula or algorithm. A signature match to a database can be a match determined by following or applying a decision tree, a rule-based system, a heuristic algorithm, a neural network or machine learning algorithm, a statistical formula, etc.

The dispensing analysis system 701 determines whether each medication placed into the system is correct for the patient. The apparatus 701 includes a central processor 708 that can receive, process, and transmit data. In some embodiments, the dispensing analysis system 701 is a computer in communication with the apparatus 100. The user of the apparatus 100 can enter patient identifier information (e.g., name, patient ID code, etc.) into the apparatus 100 regarding the particular patient to whom the medication is to be administered. The user can enter this data via a user interface of the apparatus, via a computer connected to the apparatus, by scanning a code on the patient file, by retrieving an electronic record for the patient, or via another mechanism. The central processor 708 can receive the patient identifier information and use this to determine who the patient is and/or link to the patient's medical records. The medication prescriptions for a patient are programmed into the apparatus 100, or the apparatus 100 communicates with an electronic medical record system to obtain the prescription information for a patient. The central processor 708 can further manage this acquiring of prescription information.

The dispensing analysis system 701 checks each medication placed into the apparatus against the patient's prescriptions and a record of medications previously administered to the patient. For medications that are missing from the prescription record or incorrect for the patient, the central processor 708 can generate an indication to reject the medication. For medications that match the prescription record or are correct for the patient, the central processor 708 can generate an indication to accept the medication. In comparing the medication to the prescription record, the central processor 708 can check various factors, including whether the medication is the correct type and dosage, whether the correct amount is included, whether it is the correct time and/or date for administration of that medication, etc. If any one or all of these factors are not correct, the medication can be rejected. In a further embodiment of the dispensing analysis system 701, the system can further confirm whether the medication should not be mixed with a medication that has already been dispensed, and can reject a second medication if a first medication already dispensed is likely to interact negatively with the second medication. Furthermore, in some embodiments, real-time monitoring of the patient is performed with immediate auto-calibration of dosage within physician-prescribed parameters.

The central processor 708 can further communicate the indication of whether to accept or reject the medication to the apparatus 100. The gating system 116 can respond by directing the medication to an acceptance zone or rejection zone according to the central processor's instructions. The central processor 708 can also communicate to the dispensing vessel 150 a patient identification code to be stored by the dispensing vessel 150 and used to recognize the correct patient to receive the medication. In other embodiments, the user programs the code into the dispensing vessel 150 or the dispensing vessel includes a processor and other components that interact with central processor 708 to access or retrieve the code.

The central processor 708 can also have some control over the dispensing vessel 150. In some embodiments, the central processor instructs the dispensing vessel to lock once the medication is dispensed, though as explained above, the dispensing vessel 150 can also control its own locking and unlocking and can detect when a medication is loaded into the vessel 150. In some embodiments, the dispensing vessel 750 will not lock until the central processor sends instructions to lock, and the central processor 708 can wait until all the medication types and all of the pills of each medication type for the patient to be taken at that time are dispensed. Where a user has to take a certain amount of a medication type (e.g., two pills), the pills can be placed into the guide tube at the same time or separately. If they are placed separately, the central processor 708 can prevent dispensing of the medication or can prevent removal of the dispensing vessel holding the first pill until both pills are dispensed. The central processor 708 can also receive and use data provided from the dispensing vessel 150 regarding the date/time of dispensing or administration of the medication. This can be used for tracking administrations of medication given to the patient over time, and to determine when the next dose of each medication should be administered.

The dataset for comparison of medications placed in the apparatus can include a subset of medications prescribed for the particular patient taken from the database of all known medications. Medications placed in the apparatus that do not match one of the medications in the subset of prescribed medications for that patient are rejected. The dispensing analysis system 701 can send information regarding the acceptance or rejection of a pill to the gating system 116 or to a controller operating the gating system 116. Thus, the apparatus 100 ensures that the medications for the patient that are placed into the apparatus are the correct medication, dosage strength, number, and ensures that the current time (or an administration time entered by the user) is the correct time for administering that medication to the patient, and so forth.

Medication Verification and Dispensing Methods

Verification of Medication

Figure 8:
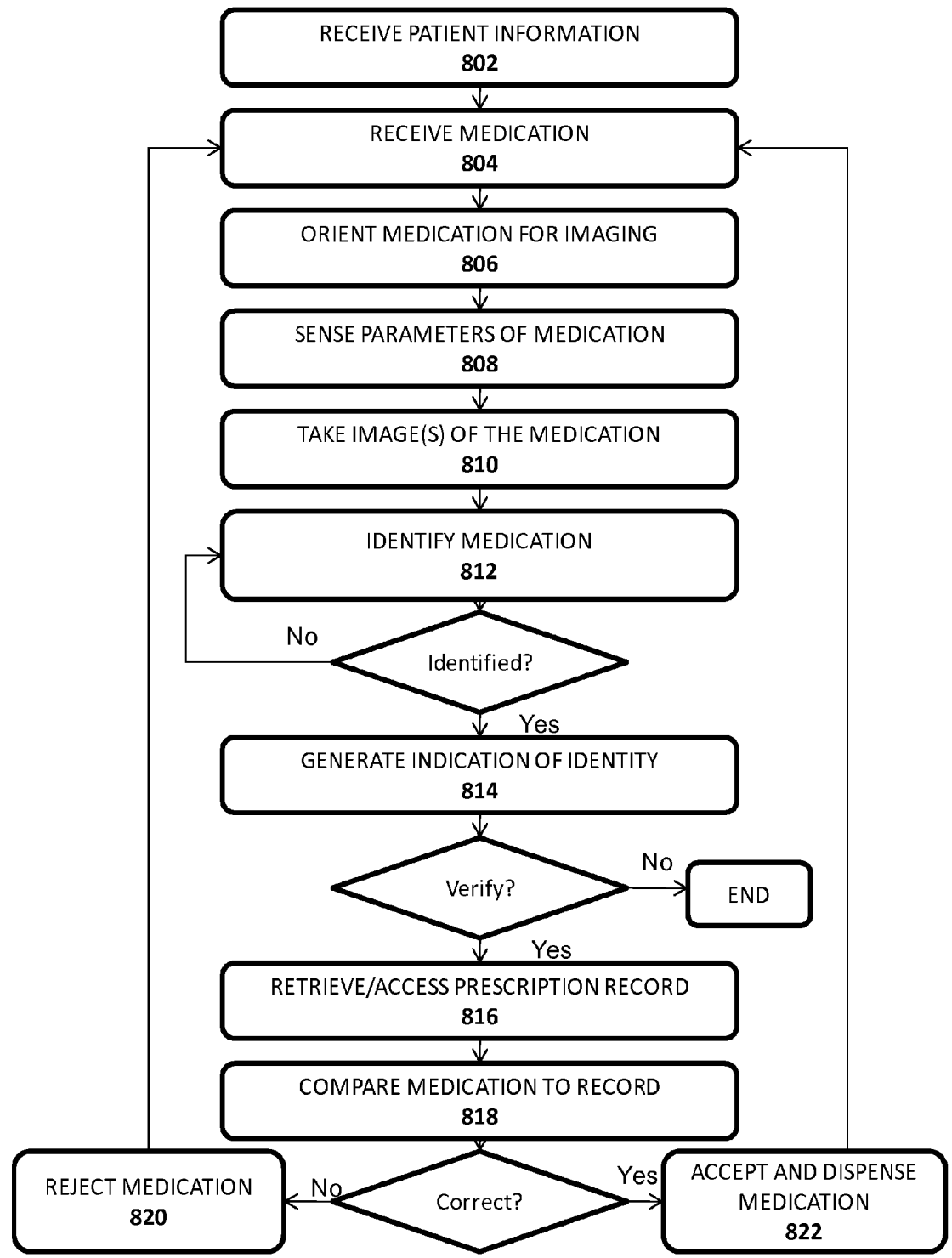
FIG. 8 is a flowchart illustrating the method of verifying a medication, in accordance with an embodiment of the invention.

FIG. 8 is a flowchart illustrating the method of verifying a medication, in accordance with an embodiment of the invention. It should be understood that these steps are illustrative only. Different embodiments of the invention may perform the illustrated steps in different orders, omit certain steps, and/or perform additional steps not shown in FIG. 8 (the same is true for FIG. 9). The method can start and end at various points in the process, and typically the method is a continuous process with multiple steps occurring simultaneously, so the Figures provide only an example of one ordering of method steps. In addition, the method can be performed using any of the apparatuses described herein or another apparatus capable of performing the steps provided below.

The verification method includes a number of steps. In one embodiment, with method includes receiving 802 identification information for a patient to whom a medication will be administered (e.g., name, medical record number, etc.). The method further includes receiving 804 a medication. In one embodiment, the medication is received in a guide tube through which the medication is delivered for dispensing, which can include any area or compartment. In some embodiments, the method includes optimally orienting 806 the medication for imaging of the medication. For example, where a guide tube is used, this can include orienting the medication via ridges or coatings in the guide tube, by the angle of positioning of the guide tube, or any of the mechanisms described above. In some embodiments, the method also includes sensing 808 one or more parameters regarding the medication (e.g., speed, velocity, etc.). The method further includes taking 810 one or more images of the medication. In addition, the method includes identifying 812 the medication. For example, the medication can be identified based on a signature of the image of the medication, by comparing the image of the medication to images of medications in a database to identify the medication, by analyzing a number of characteristics for the medication using the image or characteristics collected by sensors, etc. The method also includes generating 814 an indication of the medication identified.

In embodiments in which further verification is to be performed based on prescription records of the patient, the method includes retrieving or accessing 816 a prescription record for the patient. The method also includes comparing 818 the medication to a prescription record for the patient to verify that the medication is appropriate for the patient. In some embodiments, the medication will be accepted or rejected based on input from the verification system 120. If the medication is determined to be correct for the patient, it is accepted and dispensed 822 for administration to the patient. The user can then enter the next medication for that same patient, and repeat the process to verify that the next medication is correct. The user can continue this process until all medications for the patient to be taken at that time are dispensed. If the medication is found not to be correct for the patient (e.g., incorrect type, dosage, amount, strength, timing, etc.), it is rejected 820 and is not dispensed for administration, but instead can be routed to a rejection zone or otherwise labeled rejected. The user can re-enter a different medication in which case the method begins again with the guide tube receiving 804 the medication.

Dispensing of Medication

Figure 9:
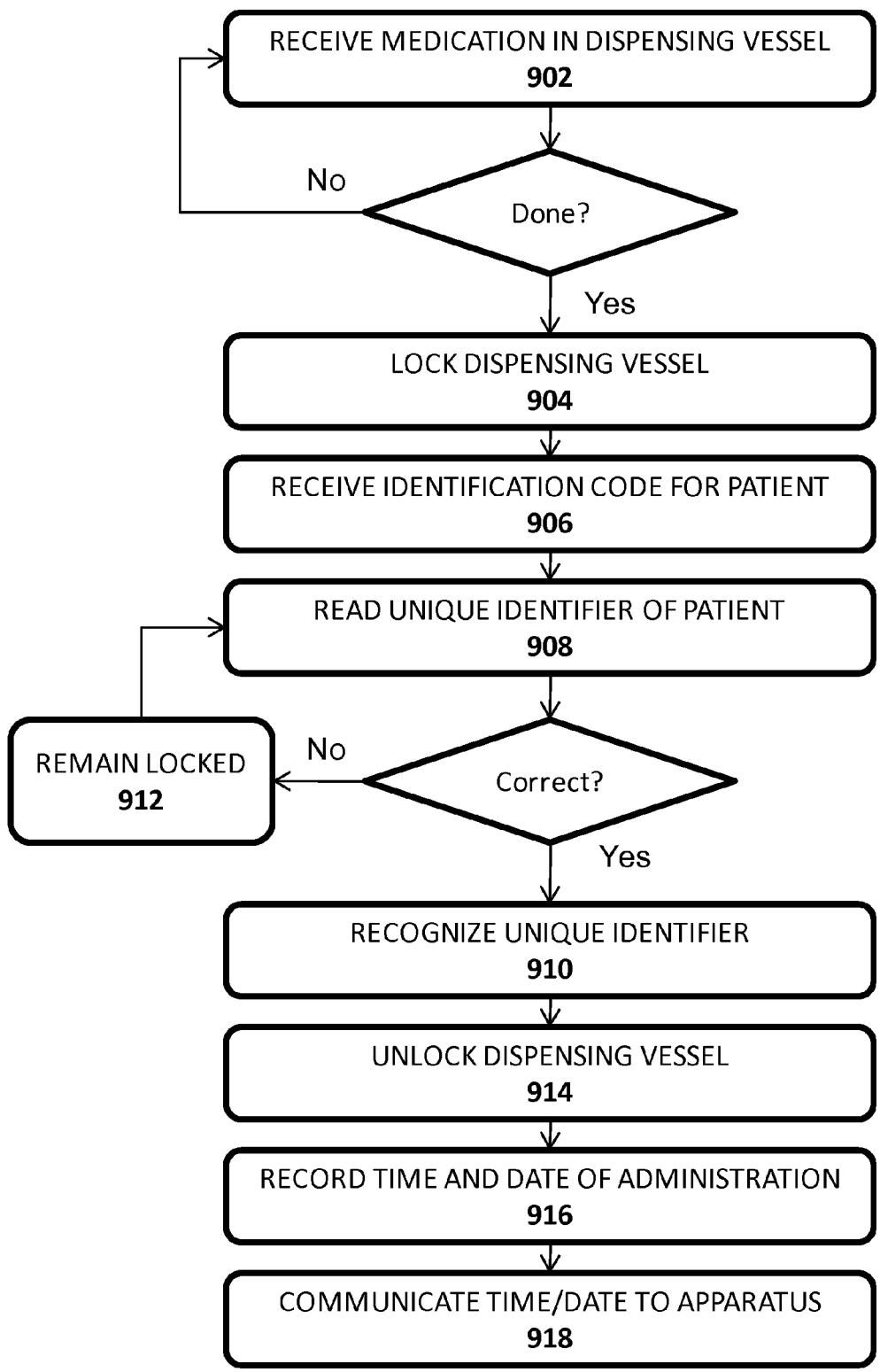
FIG. 9 is a flowchart illustrating the method of dispensing a medication, in accordance with an embodiment of the invention.

FIG. 9 is a flowchart illustrating the method of dispensing a medication, in accordance with an embodiment of the invention. The method includes receiving 902 a medication in a dispensing vessel. If additional medications are to be dispensed for that same patient, the dispensing vessel can receive 902 more medications. Once the dispensing vessel has received 902 all the medications to be received at that time, the dispensing vessel locks 904 the medication inside. The method also includes receiving 906 an identification code for the patient to whom the medication should be dispensed. In addition, the method includes reading 908 a unique identifier for a patient to whom the medication may be administered (e.g., in response to being in proximity to a patient to whom the medication is to be administered). If the identifier is the identifier for the correct recipient of the medication, the method includes recognizing 910 the unique identifier for the patient. If the identifier is not the identifier for the correct recipient, the dispensing vessel remains 912 locked. The method further includes unlocking 914 the dispensing vessel to provide access to the medication for the patient in response to the recognition of the unique identifier for the patient. In some embodiments, the method includes recording 916 the time/date of administration of the medication, and communicating 918 this information to a computer or apparatus (e.g., the medication verification apparatus 102) that tracks this information for timing future administration of medications to the patient.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure. The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

We claim:

1. A medication verification apparatus comprising:
   a guide tube having an entry area on a first end for receiving a medication and at least one exit area on a second end for providing the medication;
   a plurality of imaging devices positioned adjacent to an imaging zone of the guide tube and arranged for taking a plurality of images from different perspectives of the medication within the imaging zone while the medication is in motion within the guide tube from the entry area on the first end through the imaging zone towards the at least one exit area;
   a light source for providing illumination to the medication while the medication is being imaged in the imaging zone;
   a proximity sensor to detect the presence of the medication and set proper timing for the plurality of imaging devices and the light source;
   a verification system in communication with the imaging device for comparing the plurality of images of the medication to a plurality of images of medications in a database to identify the medication, wherein the verification system is configured for standardizing the plurality of different perspective images of the medication, comparing the standardized different perspective images of the medication to the plurality of images of medications in the database, and identifying the medication based on the comparing; and
   an output system in communication with the verification system for generating an indication of the medication identified,
   wherein the plurality of imaging devices are a) arranged circumferentially around the imaging zone of the guide tube, b) coupled to a mechanism for moving the imaging devices, or c) arranged opposite a plurality of mirrors positioned around the imaging zone.

2. The apparatus of claim 1, wherein the verification system is configured for standardizing the plurality of different perspective images of the medication by determining, from the plurality of different perspective images of the medication, a set of characteristics of the medication.

3. The apparatus of claim 2, wherein the verification system is configured for comparing the standardized different perspective images of the medication to the plurality of images of medications in the database by comparing the determined characteristics of the medication to characteristics of the plurality of images of medications in the database.

4. The apparatus of claim 3, wherein the verification system is further configured for determining the set of characteristics of the medication by performing one or more of 1) optical recognition of characters embossed, debossed, engraved or printed on the medication, 2) optical recognition of identifying markings, such as trademark letters, marks, symbols, internal and external cut outs, 3) a comparison of characters and markings to a database containing known characters and markings, 4) an analysis of the medications structural properties (e.g. shape, color, size, scoring), and 5) an analysis of medication physical properties.

5. The apparatus of claim 2, wherein the determined characteristics of the medication comprise one or more of: a color or coloration pattern, one or more markings, a volume, a shape, a size, a shading, or a texture.

6. The apparatus of claim 2, wherein the determined characteristics comprise one or more structural or physical properties of the medication.

7. The apparatus of claim 1, wherein the verification system further comprises:
   a medication identification system that includes an image analyzer for analyzing the plurality of different perspective images and comparing the plurality of different perspective images to the plurality of images in the database; and
   a dispensing analysis system for comparing the medication identified by the medication identification system to a prescription record of a patient to verify that the medication is appropriate for the patient.

8. The apparatus of claim 7, wherein the dispensing analysis system is adapted to make a determination selected from a group consisting of: a) whether the medication is a correct medication to be administered to the patient, b) whether the medication is of a correct dosage to be administered to the patient, c) whether the medication is of a correct strength to be administered to the patient, and d) whether a time for administering the medication is a correct time for administration of the medication to the patient.

9. The apparatus of claim 1, further comprising a gating system mounted to the guide tube and positioned to accept or reject the medication based on input received from the verification system, the gating system comprising a gating mechanism for routing the medication to different pathways in the guide tube.

10. The apparatus of claim 9, wherein the gating mechanism is selected from a group consisting of: a) a plunger air gate for pushing the pill toward or away from a rejection or acceptance zone, b) an accept/reject gate adapted to swing within the guide tube to direct the medication to a rejection or acceptance zone, and c) a holding gate for receiving and holding medication while it is determined whether the medication is accepted or rejected.

11. The apparatus of claim 1, wherein the light source comprises a plurality of light sources positioned adjacent to the imaging zone for illuminating the medication during imaging.

12. The apparatus of claim 11, wherein the plurality of light sources are positioned to surround a field of view of the plurality of imaging devices, with an incident light path of the light sources raised or recessed and at an acute angle with respect to a plane containing the medication.

13. The apparatus of claim 11, wherein the plurality of light sources comprise a) a plurality of light sources positioned above or below the medication and projecting at an acute angle of incidence to a plane of the medication, or b) a plurality of light sources positioned on a side of the medication and projecting at an acute angle of incidence to the medication.

14. The apparatus of claim 1, wherein the verification system is configured for standardizing the plurality of different perspective images of the medication by determining, from the plurality of different perspective images of the medication, a signature or fingerprint of the medication.

15. The apparatus of claim 14, wherein the verification system is configured for comparing the standardized different perspective images of the medication to the plurality of images of medications in the database by comparing the signature or fingerprint of the medication to signatures or fingerprints of the plurality of images of medications in the database.

16. The apparatus of claim 1, wherein the sensor is positioned adjacent to a trigger zone of the guide tube for recording information about the pill as it passes through the guide tube to set a proper timing for taking the plurality of images of the medication or providing light in the imaging zone.

17. The apparatus of claim 1, further comprising a dispensing vessel having an opening for receiving the medication from the guide tube, a lid, an identification system programmable with an identification code for a particular patient to whom the medication is to be administered, and a locking mechanism adapted to lock the lid closed and to unlock responsive to the identification system recognizing a unique identifier for the particular patient.

18. The apparatus of claim 1, wherein an internal surface of a passage of the guide tube comprises: a) one or more ridges, grooves, indentations, bumps or discontinuities, or b) one or more coatings that adjust a coefficient of friction between the guide tube and the medication moving through the guide tube, wherein a) and b) are configured to control orientation, position, translational velocity or angular velocity of the medication as it moves through the guide tube.

19. The apparatus of claim 1, wherein the guide tube includes a gaseous system for providing a gas inside the guide tube or a mechanical device for adjusting movement, orientation, position, translational velocity, or angular velocity of the medication, wherein the mechanical device is selected from a group consisting of: a vibration device, a conveyor belt, and a plunger.

20. The apparatus of claim 1, wherein the guide tube is oriented at approximately 5 to 89 degrees to a force of gravity or other external force exerted on the medication.

21. The apparatus of claim 1, wherein the guide tube is positioned at an angle relative to a force of gravity to orient a long axis of the medication in a direction of travel through the guide tube or with a long axis of the guide tube, and to orient the medication face down, wherein the guide tube is configured for allowing the medication to slide through the imaging zone of the guide tube.

22. The apparatus of claim 1, wherein the plurality of light sources are oriented around the imaging zone and timed or coordinated with one another to provide high-contrast illumination of embossed, debossed, or engraved features on the medication, printed markings on a surface of the medication, and color, shape, and size of the medication.

23. The apparatus of claim 1, wherein the plurality of light sources are positioned around the imaging zone to provide incident light reflected off an indented or raised edge of embossed or debossed markings on the medication or reflected off a surface, a valley, or a peak of the embossed or debossed markings.

24. The apparatus of claim 1, wherein the plurality of light sources are oriented around the imaging zone with at least one light source providing direct illumination for imaging printed markings on the medication and at least one light source providing tangential illumination for enhancing contrast of surface features of the medication.

25. The apparatus of claim 1, wherein the verification system is configured for comparing the standardized different perspective images of the medication to the plurality of images of medications in the database using one or more of: a decision tree, a rule-based system, a heuristic algorithm, a neural network algorithm, a machine learning algorithm, or a statistical formula.

26. The apparatus of claim 1, wherein the plurality of imaging devices are arranged circumferentially around the imaging zone of the guide tube.

27. The apparatus of claim 1, wherein the plurality of imaging devices are coupled to a mechanism for moving the imaging devices.

28. The apparatus of claim 1, wherein the plurality of imaging devices are arranged opposite a plurality of mirrors positioned around the imaging zone.

29. A method of medication verification comprising:
receiving a medication provided through a guide tube having an entry area on a first end for receiving a medication and at least one exit area on a second end for providing the medication;
detecting with a sensor the presence of the medication to set proper timing for imaging the medication;
taking a plurality of images of the medication from different perspectives of the medication within an imaging zone of the guide tube while the medication is in motion within the guide tube, the images taken with a plurality of imaging devices positioned adjacent to the imaging zone of the guide tube and arranged for taking the images as the medication traveling from the entry area on the first end through the imaging zone towards the at least one exit area, the proper timing of the imaging devices set based on the detection of the medication by the sensor, wherein the plurality of imaging devices are a) arranged circumferentially around the imaging zone of the guide tube, b) coupled to a mechanism for moving the imaging devices, or c) arranged opposite a plurality of mirrors positioned around the imaging zone;
illuminating the medication with a light source while the medication is being imaged in the imaging zone, the timing of the light source set based on the detection of the medication by the sensor;
identifying the medication based on the plurality of images taken of the medication, the identification comprising:
determining a set of characteristics of the medication from the different perspective images of the medication,
comparing the determined characteristics of the medication to a set of characteristics for each of a plurality of images of medications stored in a database, and
identifying the medication based on the comparing; and
generating an indication of the medication identified.

30. The method of claim 29, further comprising:
retrieving or accessing a prescription record for a patient; and
comparing the medication identified to the prescription record of the patient to verify that the medication is appropriate for the patient.

31. The method of claim 30, further comprising accepting or rejecting the medication based on whether the medication matches a prescription record of the patient, wherein the medication is accepted if it matches and rejected if it does not match.

32. The method of claim 29, further comprising adjusting an orientation of the medication to position the medication for imaging.

33. The method of claim 29, further comprising further comprising sensing a presence, speed, velocity, or orientation of the medication as it moves through an area.

34. The method of claim 29, wherein illuminating the medication further comprises illuminating the medication using a plurality of light sources, wherein the imaging devices and light sources are oriented and timed for providing images that reveal one or more markings on the medication and at least one of the color, shape, and size of the medication.

35. The method of claim 29, wherein identifying further comprises comparing the image of the medication to a plurality of images of medications to identify the medication.

36. A medication verification apparatus comprising:
a guide tube having an entry area on a first end for receiving a medication and at least one exit area on a second end for providing the medication;
a plurality of imaging devices positioned adjacent to an imaging zone of the guide tube and arranged for taking a plurality of images from different perspectives of the medication within the imaging zone while the medication is in motion within the guide tube from the entry area on the first end through the imaging zone towards the at least one exit area;
a light source for providing illumination to the medication while the medication is being imaged in the imaging zone;
a proximity sensor to detect the presence of the medication and set proper timing for the plurality of imaging devices and the light source;
a verification system in communication with the imaging device for identifying the medication based on the plurality of images taken of the medication, wherein the verification system is configured for determining a set of characteristics of the medication from the different perspective images of the medication, comparing the determined characteristics of the medication to a set of characteristics for each of a plurality of medications stored in the database, and identifying the medication based on the comparing; and
an output system in communication with the verification system for generating an indication of the medication identified,
wherein the plurality of imaging devices are a) arranged circumferentially around the imaging zone of the guide tube, b) coupled to a mechanism for moving the imaging devices, or c) arranged opposite a plurality of mirrors positioned around the imaging zone.

37. The apparatus of claim 36, wherein the verification system further comprises:
a medication identification system that includes an image analyzer for analyzing the set of characteristics of the medication determined from the different perspective images of the medication and comparing the determined characteristics of the medication to a set of characteristics for each of a plurality of medications stored in the database; and
a dispensing analysis system for comparing the medication identified by the medication identification system to a prescription record of a patient to verify that the medication is appropriate for the patient.

38. The apparatus of claim 37, wherein the dispensing analysis system is adapted to make a determination selected from a group consisting of: a) whether the medication is a correct medication to be administered to the patient, b) whether the medication is of a correct dosage to be administered to the patient, c) whether the medication is of a correct strength to be administered to the patient, and d) whether a time for administering the medication is a correct time for administration of the medication to the patient.

39. The apparatus of claim 36, further comprising a gating system mounted to the guide tube and positioned to accept or reject the medication based on input received from the verification system, the gating system comprising a gating mechanism for routing the medication to different pathways in the guide tube.

40. The apparatus of claim 39, wherein the gating mechanism is selected from a group consisting of: a) a plunger air gate for pushing the pill toward or away from a rejection or acceptance zone, b) an accept/reject gate adapted to swing within the guide tube to direct the medication to a rejection or acceptance zone, and c) a holding gate for receiving and holding medication while it is determined whether the medication is accepted or rejected.

41. The apparatus of claim 36, wherein the light source comprises a plurality of light sources positioned adjacent to the imaging zone for illuminating the medication during imaging.

42. The apparatus of claim 41, wherein the plurality of light sources are positioned to surround a field of view of the plurality of imaging devices, with an incident light path of the light sources raised or recessed and at an acute angle with respect to a plane containing the medication.

43. The apparatus of claim 41, wherein the plurality of light sources comprise a) a plurality of light sources positioned above or below the medication and projecting at an acute angle of incidence to a plane of the medication, or b) a plurality of light sources positioned on a side of the medication and projecting at an acute angle of incidence to the medication.

44. The apparatus of claim 36, wherein the sensor is positioned adjacent to a trigger zone of the guide tube for recording information about the pill as it passes through the guide tube to set a proper timing for taking the plurality of images of the medication or providing light in the imaging zone.

45. The apparatus of claim 36, further comprising a dispensing vessel having an opening for receiving the medication from the guide tube, a lid, an identification system programmable with an identification code for a particular patient to whom the medication is to be administered, and a locking mechanism adapted to lock the lid closed and to unlock responsive to the identification system recognizing a unique identifier for the particular patient.

46. The apparatus of claim 36, wherein an internal surface of a passage of the guide tube comprises: a) one or more ridges, grooves, indentations, bumps or discontinuities, or b) one or more coatings that adjust a coefficient of friction between the guide tube and the medication moving through the guide tube, wherein a) and b) are configured to control orientation, position, translational velocity or angular velocity of the medication as it moves through the guide tube.

47. The apparatus of claim 36, wherein the guide tube includes a gaseous system for providing a gas inside the guide tube or a mechanical device for adjusting movement, orientation, position, translational velocity, or angular velocity of the medication, wherein the mechanical device is selected from a group consisting of: a vibration device, a conveyor belt, and a plunger.

48. The apparatus of claim 36, wherein the guide tube is oriented at approximately 5 to 89 degrees to a force of gravity or other external force exerted on the medication.

49. The apparatus of claim 36, wherein the guide tube is positioned at an angle relative to a force of gravity to orient a long axis of the medication in a direction of travel through the guide tube or with a long axis of the guide tube, and to orient the medication face down, wherein the guide tube is configured for allowing the medication to slide through the imaging zone of the guide tube.

50. The apparatus of claim 36, wherein the plurality of light sources are oriented around the imaging zone and timed or coordinated with one another to provide high-contrast illumination of embossed, debossed, or engraved features on the medication, printed markings on a surface of the medication, and color, shape, and size of the medication.

51. The apparatus of claim 36, wherein the plurality of light sources are positioned around the imaging zone to provide incident light reflected off an indented or raised edge of embossed or debossed markings on the medication or reflected off a surface, a valley, or a peak of the embossed or debossed markings.

52. The apparatus of claim 36, wherein the plurality of light sources are oriented around the imaging zone with at least one light source providing direct illumination for imaging printed markings on the medication and at least one light source providing tangential illumination for enhancing contrast of surface features of the medication.

53. The apparatus of claim 36, wherein the determined characteristics of the medication comprise one or more of: a color or coloration pattern, one or more markings, a volume, a shape, a size, a shading, or a texture.

54. The apparatus of claim 36, wherein the determined characteristics comprise one or more structural or physical properties of the medication.

55. The apparatus of claim 36, wherein the determined characteristics of the medication comprise one or more of 1) optical recognition of characters embossed, debossed, engraved or printed on the medication, 2) optical recognition of identifying markings, such as trademark letters, marks, symbols, internal and external cut outs, 3) a comparison of characters and markings to a database containing known characters and markings, 4) an analysis of the medications structural properties (e.g. shape, color, size, scoring), and 5) an analysis of medication physical properties.

56. The apparatus of claim 36, wherein the verification system is configured for comparing the determined characteristics of the medication to a set of characteristics for each of a plurality of medications stored in the database using one or more of: a decision tree, a rule-based system, a heuristic algorithm, a neural network algorithm, a machine learning algorithm, or a statistical formula.

57. The apparatus of claim 36, wherein the plurality of imaging devices are arranged circumferentially around the imaging zone of the guide tube.

58. The apparatus of claim 36, wherein the plurality of imaging devices are coupled to a mechanism for moving the imaging devices.

59. The apparatus of claim 36, wherein the plurality of imaging devices are arranged opposite a plurality of mirrors positioned around the imaging zone.

* * * * *